United States Patent [19]

Otsuka

[11] Patent Number: 5,296,519
[45] Date of Patent: Mar. 22, 1994

[54] INDOLE COMPOUND AND USE OF THE SAME
[75] Inventor: Masahiro Otsuka, Osaka, Japan
[73] Assignee: Orient Chemical Industries, Ltd., Osaka, Japan
[21] Appl. No.: 897,103
[22] Filed: Jun. 11, 1992

Related U.S. Application Data

[62] Division of Ser. No. 765,201, Sep. 25, 1991, abandoned.

[30] Foreign Application Priority Data

Sep. 25, 1990 [JP] Japan .................................. 2-256036

[51] Int. Cl.$^5$ .................. C07D 209/12; C07D 209/14; A61K 7/04
[52] U.S. Cl. .................. 524/94; 252/299.01; 430/931; 424/59; 548/494; 548/505
[58] Field of Search ............... 252/89; 548/494, 505

[56] References Cited

U.S. PATENT DOCUMENTS 3,109,844 11/1963 Perron et al. ................ 548/494
4,522,808 6/1985 Jacquet et al. ................ 548/494

FOREIGN PATENT DOCUMENTS 2152995 4/1973 France ................ 548/494

OTHER PUBLICATIONS

CA 54:7683; Sixth Collective Index, 1957, 2638f.
CA 110(23):212675p, Hiremath, 1989, 2662f; 2210f; 2514f.

Primary Examiner—Mary C. Lee
Assistant Examiner—Joseph K. McKane
Attorney, Agent, or Firm—Birch, Stewart, Kolasch & Birch

[57] ABSTRACT

Disclosed is a novel UV light absorbing compound which can preferably be employed in the art of colored molding plastics, resin films, heat-sensitive transfer materials, liquid crystal display materials, color photographs and the like, and method for producing thereof. The UV light absorbing compound is characterized by the general formula:

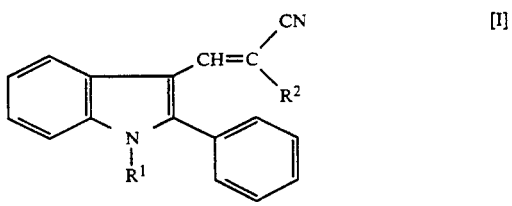

wherein $R^1$ represents linear or branched alkyl or aralkyl group, and $R^2$ represents —CN or —COOR$^3$, wherein $R^3$ represents substituted or unsubstituted alkyl or aralkyl group.

4 Claims, 7 Drawing Sheets

INDOLE COMPOUND AND USE OF THE SAME

This application is a divisional of copending application Ser. No. 07/765,201, filed on Sep. 25, 1991, now abandoned, the entire contents of which are hereby incorporated by reference.

FIELD OF THE INVENTION

The present invention relates to a novel indole compound which is quite useful as a UV light absorbing additive or an anti-halation additive for colored resin compositions, resin films, heat-sensitive recording materials, liquid crystal display materials and the like.

BACKGROUND OF THE INVENTION

UV light is electromagnetic radiation having a wavelength between about 250 nm and about 400 nm. A number of organic compounds are decomposed or degraded by exposure to the UV light.

Then, a wide variety of UV light absorbers are generally incorporated into the commercial organic products such as polymeric materials (e.g. natural or synthetic resin and rubber), dyes, cosmetic creams and the like to prevent the degradation of the product such as discoloration, the suntan of skin, and the like.

In recent years, the UV light absorbers are incorporated into the heat-sensitive materials widely used as heat-sensitive transfer recording materials for recording devices such as facsimiles and printers to improve the light-resistance of the heat-sensitive transfer recording materials. The UV light absorbers may also be incorporated into the liquid crystal material widely used as display materials for watches and electric calculators, meters for cars, and the like. Furthermore, there is a proposal of the method for improving the light-resistance of the color photographic image using a UV light absorber containing transparent film. Wherein, the transparent film is super-imposed onto the printed surface of the photograph as a protective UV filter layer.

Examples of the conventional UV light absorbers include salicylates, benzophenones, benzotriazoles, cyanoacrylates and hindered amines. Since much of the compounds are substantially colorless, the incorporation of the UV light absorbers into the products does not affect a transparency or a color of the products.

Most of these conventional UV light absorbers, however, absorb the UV light of the wavelength ranging between about 290 nm and about 380 nm. There have been no conventional appropriate UV light absorbers which exhibits effective absorptivity in the spectral area ranging between about 380 nm and about 400 nm.

SUMMARY OF THE INVENTION

An object of the present invention is to provide a novel UV light absorbing compound which can preferably be employed in the art of colored molding plastics, resin films, heat-sensitive transfer materials, liquid crystal display materials, color photographs and the like, and a method for producing thereof.

Another object of the present invention is to provide a UV light absorber comprising the abovementioned UV light absorbing compound as an active ingredient, and to provide a resin composition comprising the UV light absorber.

In this application, "UV light absorber" means a UV light absorbing composition containing at least one UV light absorbing compound such as an indole compound.

According to the present invention, the UV light absorbing compounds having:

a) compatibility with wide variety of the organic materials;

b) heat-stability (i.e. The UV light absorbing compounds are stable at the thermal molding temperature of the plastic products, or at the thermal transfer temperature of the heat-sensitive transfer recording products.);

c) light-resistance (i.e. The UV light absorbing compounds neither decompose under photoirradiation as radical species which react with other components contained in the commercial products, nor act under photoirradiation as photosensitizers which activate other components contained in the commercial products.); and d) efficient UV light absorptivity in the long wavelength UV light spectral area (i.e. The UV light absorbing compounds have molecular absorptivity coefficient ($\epsilon$) grater than $2.5 \times 10^4$ at maximum absorption wavelength ($\lambda_{max}$) which exists in the spectral range between about 380 nm and about 400 nm.), as well as substantial transparency; are provided.

DETAILED DESCRIPTION OF THE INVENTION

Figure 1:
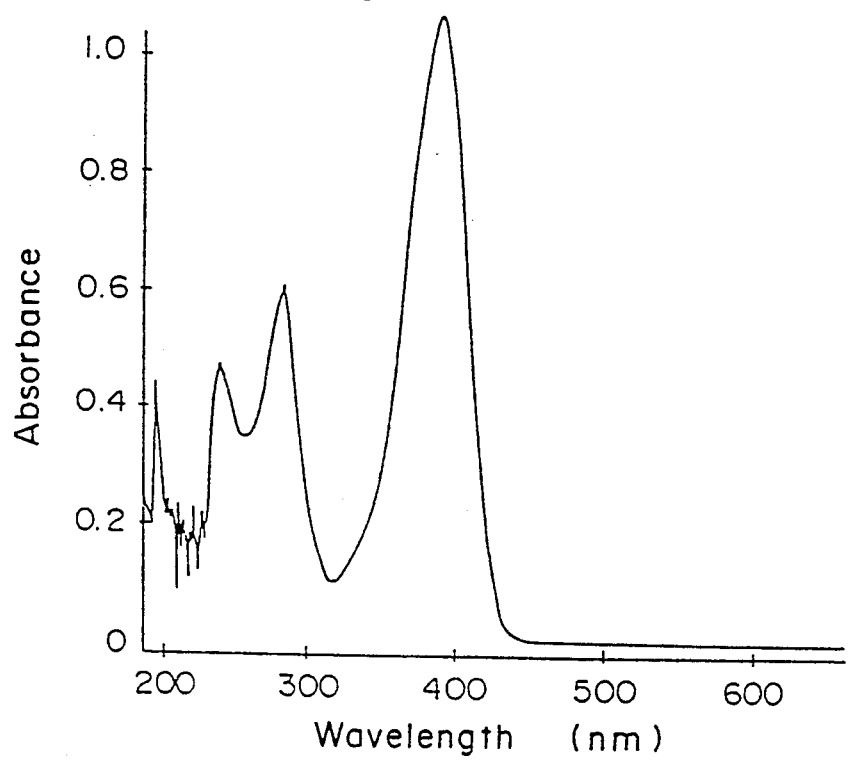
FIG. 1 is a near UV-visible light absorption spectrum of the compound 1 according to the present invention.
Figure 2:
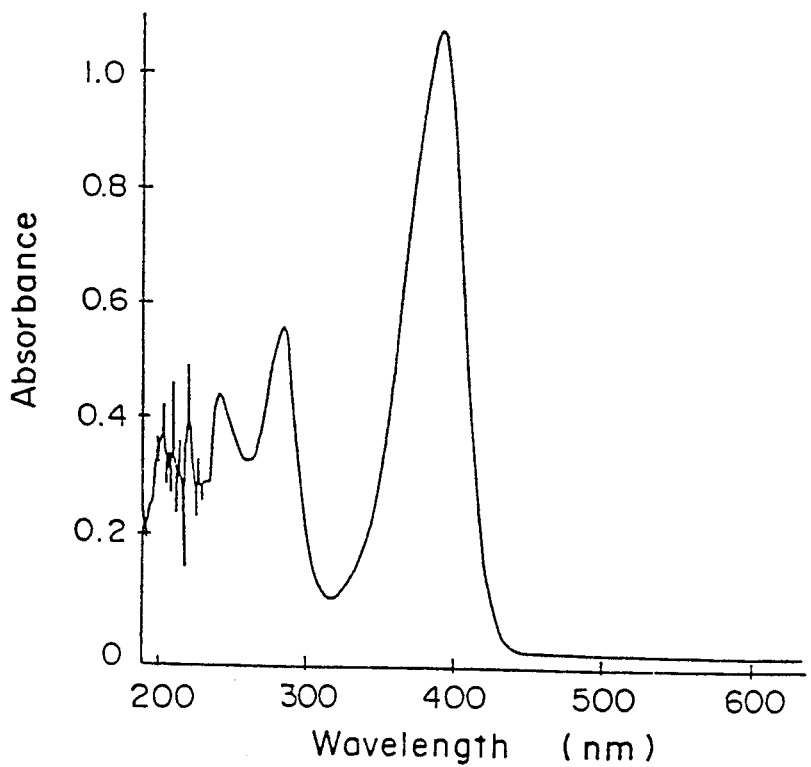
FIG. 2 is a near UV-visible light absorption spectrum of the compound 2 according to the present invention.
Figure 3:
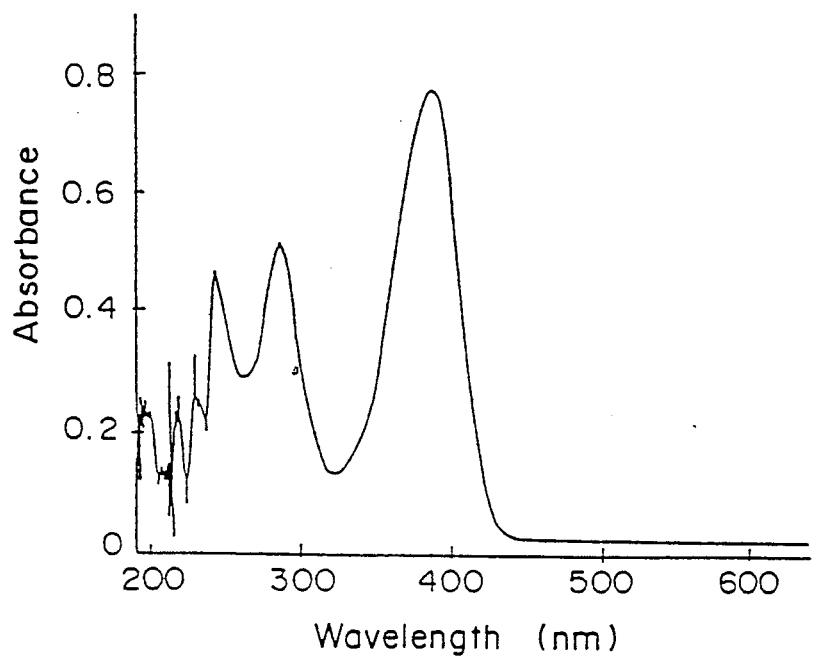
FIG. 3 is a near UV-visible light absorption spectrum of the compound 6 according to the present invention.
Figure 4:
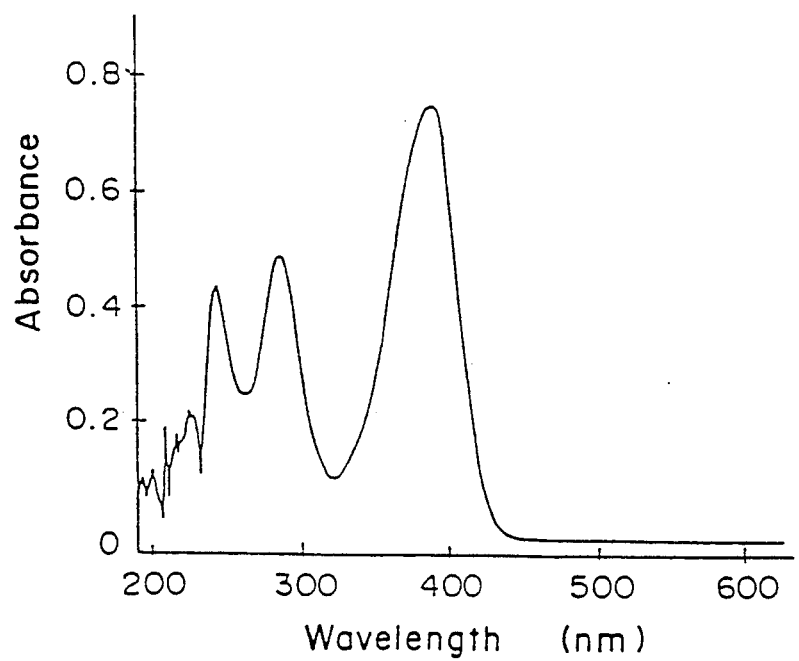
FIG. 4 is a near UV-visible light absorption spectrum of the compound 7 according to the present invention.
Figure 5:
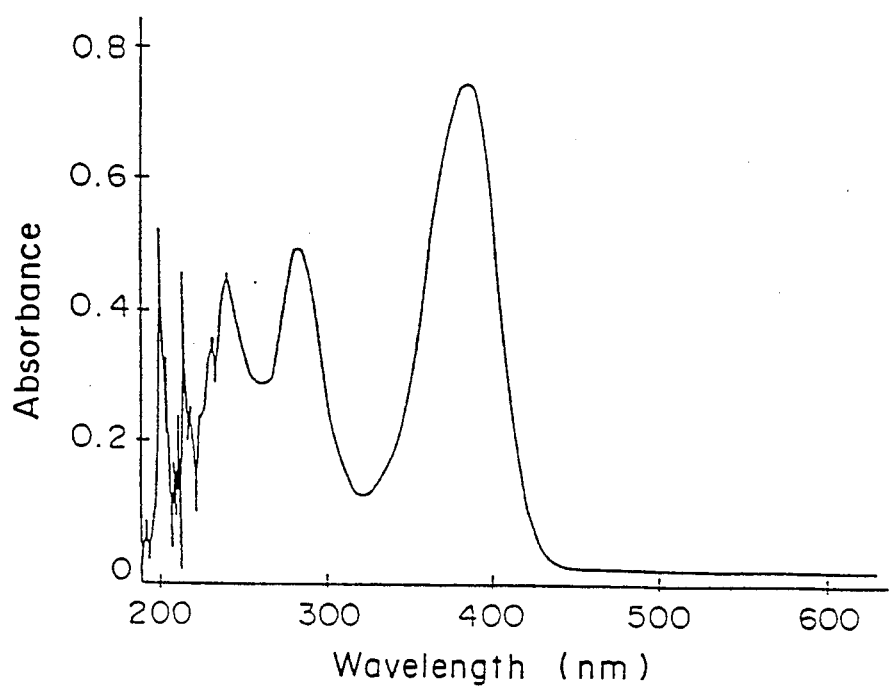
FIG. 5 is a near UV-visible light absorption spectrum of the compound 10 according to the present invention.

The UV light absorbing compound according to the present invention is an indole compound of the general formula:

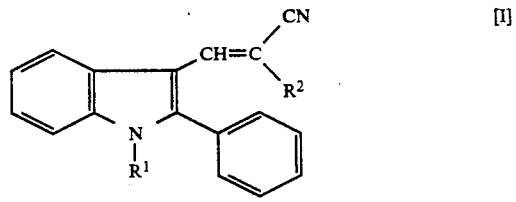

[I]

wherein $R^1$ represents linear or branched alkyl or aralkyl group, and $R^2$ represents —CN or —COOR$^3$, wherein $R^3$ represents substituted or unsubstituted alkyl or aralkyl group.

Preferably, $R^1$ of the general formula I represents a linear or branched alkyl or aralkyl group having 1-12 carbon atoms. More preferably, $R^1$ of the general formula I is selected from the group consisting of methyl, ethyl, butyl, isobutyl, t-butyl, hexyl, octyl, 2-ethylhexyl, dodecyl and benzyl group. Preferably, $R^3$ represents substituted or unsubstituted alkyl or aralkyl group having 1-20 carbon atoms. More preferably, $R^3$ is selected from the group consisting of $R^1$, β-cyanoethyl, β-chloroethyl, ethoxypropyl, hydroxyalkyl and alkoxyalkyl group.

The process for producing the indole compound according to the present invention comprises; condensing a compound of the general formula:

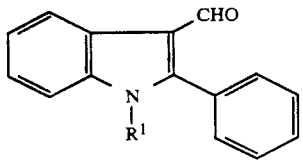  [II]

with a compound of the general formula:

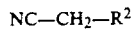  [III]

wherein $R^1$ as well as $R^2$ represent the groups as defined above respectively. Examples of the compound III include malononitrile (NC—CH$_2$—CN) and α-cyanoacetic ester (NC—CH$_2$—COOR$^3$). Wherein, $R^3$ represents the groups as defined above. Examples of the α-cyanoacetic ester include methyl cyanoacetate, ethyl cyanoacetate, isopropyl cyanoacetate, butyl cyanoacetate, t-butyl cyanoacetate, amyl cyanoacetate, octyl cyanoacetate, esters obtained from cyanoacetic acids and higher alcohols (e.g., undecyl alcohol, dodecyl alcohol, aliphatic alcohols having 13-20 carbon atoms), benzyl cyanoacetate and the like.

In the abovementioned condensation, the preferred amount of compound III is the range between 0.9-1.2 equivalent weight based on the amount of compound II. The condensation reaction may be carried out at the temperature between 10° C. and the boiling point of an employed solvent over 0.5-20 hours. The solvents employed in this reaction include alcohols (e.g., methanol, ethanol), acetic anhydride and the like. If alcohols are employed as the solvents, bases such as pyridine, triethylamine and the like can be employed as catalysts. After completion of the reaction, the compound I according to the present invention is separated and optionally purified from the reaction mixture. The separation and purification is accomplished by means known to those skilled in the art. For example, the resulting reaction mixture is poured into a solvent such as water, the precipitated compound I is then separated out from the mixture. Generally, the compound I according to the present invention may be purified by solvent (e.g. alcohols) washing, but another purification processes such as recrystallization may be employed.

The starting-compound II according to the present invention may be prepared by means known to those in the art. For example, the compound II is prepared by formylation of the following compound IV dissolved in dimethylformamide in the presence of phosphorus oxychloride (Vilsmeier reaction).

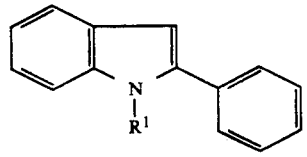  [IV]

Another procedure for preparation of compound I according to the present invention comprises, for example, condensing a compound of the general formula:

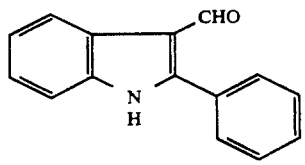  [V]

with compound III to obtain a compound of the general formula:

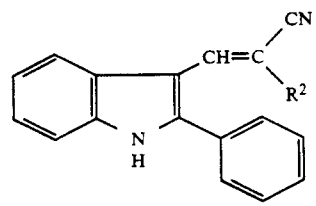  [VI]

and then, reacting the compound VI with alkylating or aralkylating agent to obtain N-alkylated or N-aralkylated compound which is compound I according to the present invention. If $R^3$ is hydrogen, compound VI may be treated with alkylating agent to obtain the derivatives thereof.

Condensation of compound V with III may be carried out in essentially the same manner as described above. N-alkylation or N-aralkylation may be conducted in usual means known to those in the art. The alkylating or aralkylating agents include alkyl or aralkyl halide (e.g., methyl iodide and benzyl iodide), dialkyl or diaralkyl sulfuric acid (e.g., dimethyl sulfuric acid and dibenzyl sulfuric acid), aromatic sulfonate and the like.

The indole compound I according to the present invention has the $\lambda_{max}$ in the spectral range between about 380 nm and about 400 nm. Thus, the long wavelength UV light may effectively be filtered out by the compound I. The compound I according to the present invention is compatible and stable with wide variety of organic materials such as organic solvents, plastics, resins and waxes, as well as has heat- and light-stability. Therefore, the indole compound I according to the present invention can preferably be employed as additive for the wide variety of resin compositions.

The resins employed in these resin compositions include polyvinyl butyrals, ethyl hydroxyethyl cellulose, stylene-maleic anhydride copolymers, methyl methacrylate resins, polyester resins, binders for heat-sensitive transfer material such as wax, plastics for molding, resins for plastic film, polymeric liquid crystals. In the photographic art, the indole compound I according to the present invention may be employed into a UV light absorbing top layer superimposed over the photographic film, or may be mixed with the colored organic materials such as color photographic pigments of dyes, so that the fastness against UV light as well as visible light of the color photographic film is improved. The indole compound I according to the present invention may be combined with the anti-halation dyes employed in the color photographic film so as to prevent the adverse effect which accompanies the exposure of the photographic film.

The indole compound I according to the present invention can be employed as UV light absorbing compound for wide variety of resin composition in an amount sufficient to provide a certain level of light resistance to the resin composition. Generally, amounts ranging from about 0.1–10% by weight and preferably about 0.5–2.0% by weight based on the solid weight of the composition can be employed. If the content of the compound I is greater than 10% by weight, a color toning deficiency may occur in colored organic compounds or in resin composition. Other conventional UV light absorbing compounds can be employed in combination with the indole compound I according to the present invention, so as to provide the wider spectral range of absorptivity. Other additives such as fluorescent whitening agents or radical scavengers may be incorporated into the resin composition according to the present invention.

EXAMPLES

The present invention will be more specifically described by the following non-limiting examples, wherein all parts are by weight unless otherwise specified.

EXAMPLES 1-11

These examples illustrate the preparation of UV light absorbing compounds according to the present invention.

Example 1

Preparation of Compound 1

The die solution was prepared by dissolving 0.10 mol of N-methyl-2-phenyl-3-indolyl aldehyde having the general formula:

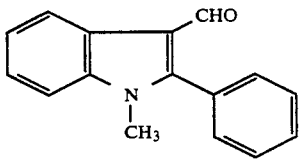

into 80 ml of ethanol. To this solution were added 0.11 mol of malononitrile, and 0.04 mol (4 parts by weight) of triethylamine. The solution was then heated to reflux, maintained at the temperature over 4 hours, and cooled to the room temperature. The resulting reaction mixture was poured into water to precipitate the condensation product. The precipitated crystals were then filtered off, washed with a little amount of alcohol, and dried to obtain the light-yellow crystals (m.p. 194°–196° C.).

Example 2

Preparation of Compound 2

The die solution was prepared by dissolving 0.10 mol of the following compound:

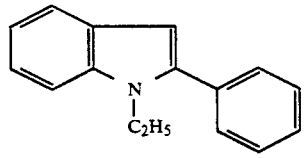

into 70 parts by weight of dimethylformamide. To this solution were then added 23 parts by weight of phosphorus oxychloride under externally cooling. Twelve parts by weight of pyridine was further added to the solution. The resulting solution was then heated to 40° C., maintained at the temperature over 1 hour and cooled to 20°–30° C. Forty parts by weight of methanol, 35 parts by weight of sodium acetate, and a solution of 6.6 parts by weight (0.1 mol) of malononitrile into 5 parts by weight of methanol were added to the cooled solution. The solution was then heated to 70° C., maintained at the temperature over 1 hour, and cooled to the room temperature. The resulting reaction mixture was poured into water to precipitate the condensation product. The precipitated crystals were then filtered off, washed with water, and dried to obtain 28.5 parts by weight of powder product. Recrystallization of the resulting powder from methyl ethyl ketone gave the light-yellow crystals (m.p. 163°–165° C.).

Example 3

Preparation of Compound 3

The light yellow crystals were obtained by essentially the same manner as described in Example 1 except that N-butyl-2-phenyl-3-indolyl aldehyde instead of N-methyl-2-phenyl-3-indolyl aldehyde, and 5 hours refluxing were used.

Example 4

Preparation of Compound 4

The light yellow powder was obtained by essentially the same manner as described in Example 1 except that N-(2-ethylhexyl)-2-phenyl-3-indolyl aldehyde instead of N-methyl-2-phenyl-3-indolyl aldehyde, and 5 hours refluxing were used.

Example 5

Preparation of Compound 5

The light yellow crystals were obtained by essentially the same manner as described in Example 1 except that N-benzyl-2-phenyl-3-indolyl aldehyde instead of N-methyl-2-phenyl-3-indolyl aldehyde, and 5 hours refluxing were used.

Example 6

Preparation of Compound 6

The light-yellow crystals (m.p. 140°–142° C.) were obtained by essentially the same manner as described in Example 1 except that ethyl cyanoacetate instead of malononitrile, and 4 hours refluxing were used.

Example 7

Preparation of Compound 7

The light yellow crystals were obtained by essentially the same manner as described in Example 1 except that butyl cyanoacetate instead of malononitrile, and 5 hours refluxing were used.

Example 8

Preparation of Compound 8

The light yellow crystals were obtained by essentially the same manner as described in Example 1 except that the combination of N-octyl-2-phenyl-3-indolyl aldehyde with ethyl cyanoacetate instead of N-methyl-2-phenyl-3-indolyl aldehyde with malononitrile, and 5 hours refluxing were used.

Example 9

Preparation of Compound 9

The light yellow crystals were obtained by essentially the same manner as described in Example 1 except that the combination of N-benzyl-2-phenyl-3-indolyl aldehyde with ethyl cyanoacetate instead of N-methyl-2-phenyl-3-indolyl aldehyde with malononitrile, and 5 hours refluxing were used.

Example 10

Preparation of Compound 10

The light yellow crystals (m.p. 128°–133° C.) were obtained by essentially the same manner as described in Example 1 except that benzyl cyanoacetate instead of malononitrile, and 5 hours refluxing were used.

Example 11

Preparation of Compound 11

The light yellow crystals were obtained by essentially the same manner as described in Example 1 except that the combination of N-benzyl-2-phenyl-3-indolyl aldehyde with benzyl cyanoacetate instead of N-methyl-2-phenyl-3-indolyl aldehyde with malononitrile, and 5 hours refluxing were used.

The structures, $\lambda$ and $\epsilon$ at the $\lambda_{max}$ of the resulting compounds 1–11 are summarized in the following Table 1.

TABLE 1

| Compounds | $R^1$ | $R^2$ | $\lambda$ max (nm)[a] | $\epsilon$ ($\times 10^4$) at $\lambda$ max |
|---|---|---|---|---|
| 1 | $CH_3$ | CN | 396 | 3.07 |
| 2 | $C_2H_5$ | CN | 394 | 3.24 |
| 3 | $C_4H_9$ | CN | 394 | 3.05 |
| 4 | $CH_2-CH(C_2H_5)-C_4H_9$ | CN | 392 | 2.96 |
| 5 | $CH_2-C_6H_5$ | CN | 398 | 3.12 |
| 6 | $CH_3$ | $COOC_2H_5$ | 390 | 2.64 |
| 7 | $CH_3$ | $COOC_4H_9$ | 390 | 2.75 |
| 8 | $C_8H_{17}$ | $COOC_2H_5$ | 390 | 2.55 |
| 9 | $CH_2-C_6H_5$ | $COOC_2H_5$ | 392 | 2.96 |
| 10 | $CH_3$ | $COOCH_2-C_6H_5$ | 392 | 2.92 |
| 11 | $CH_2-C_6H_5$ | $COOCH_2-C_6H_5$ | 394 | 3.14 |

[a] These data were obtained by the measurement of the sample solution dissolved into chloroform.

Figure 8:
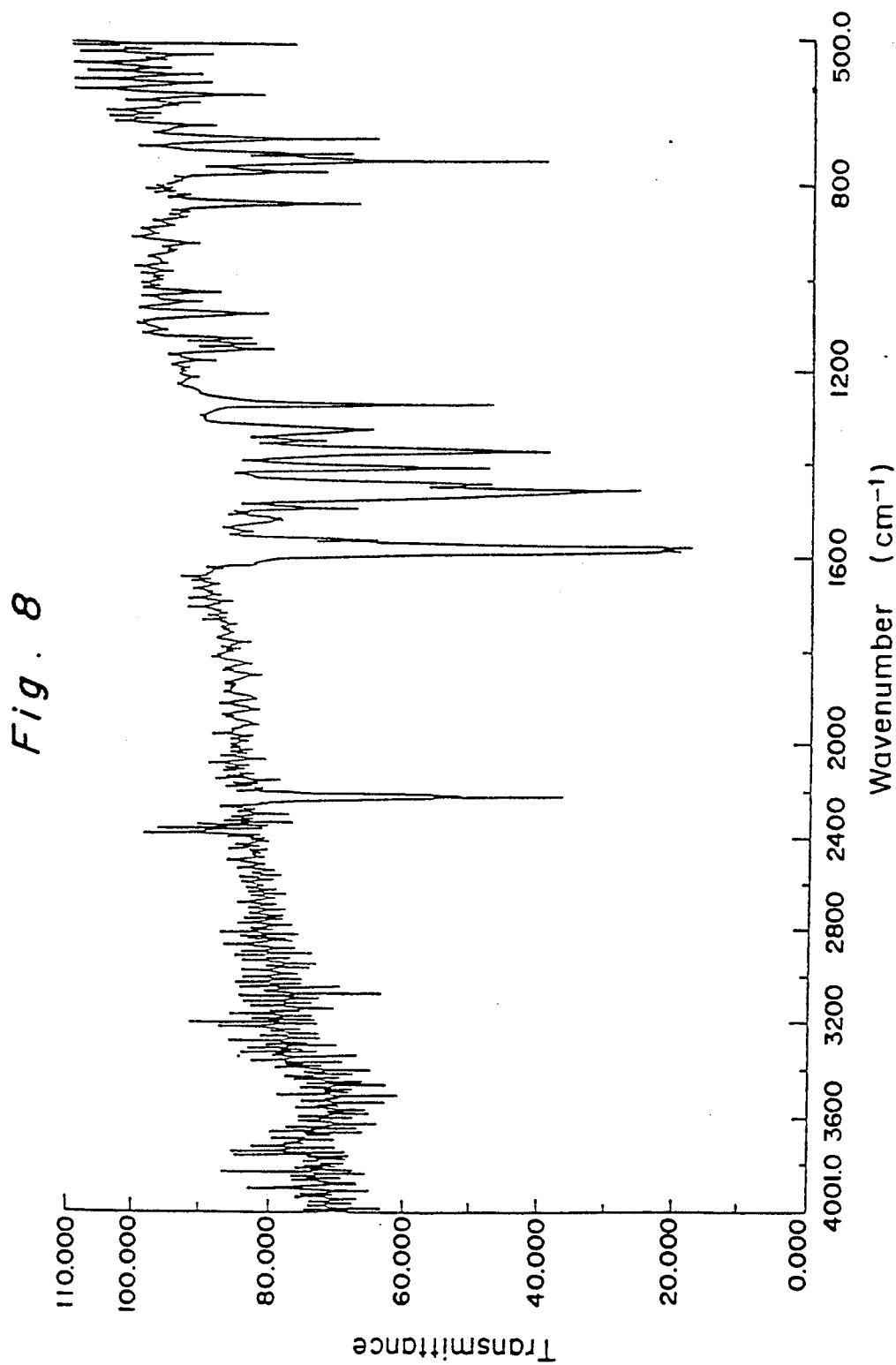
FIG. 8 is a infrared spectrum of the compound 1 according to the present invention.
Figure 9:
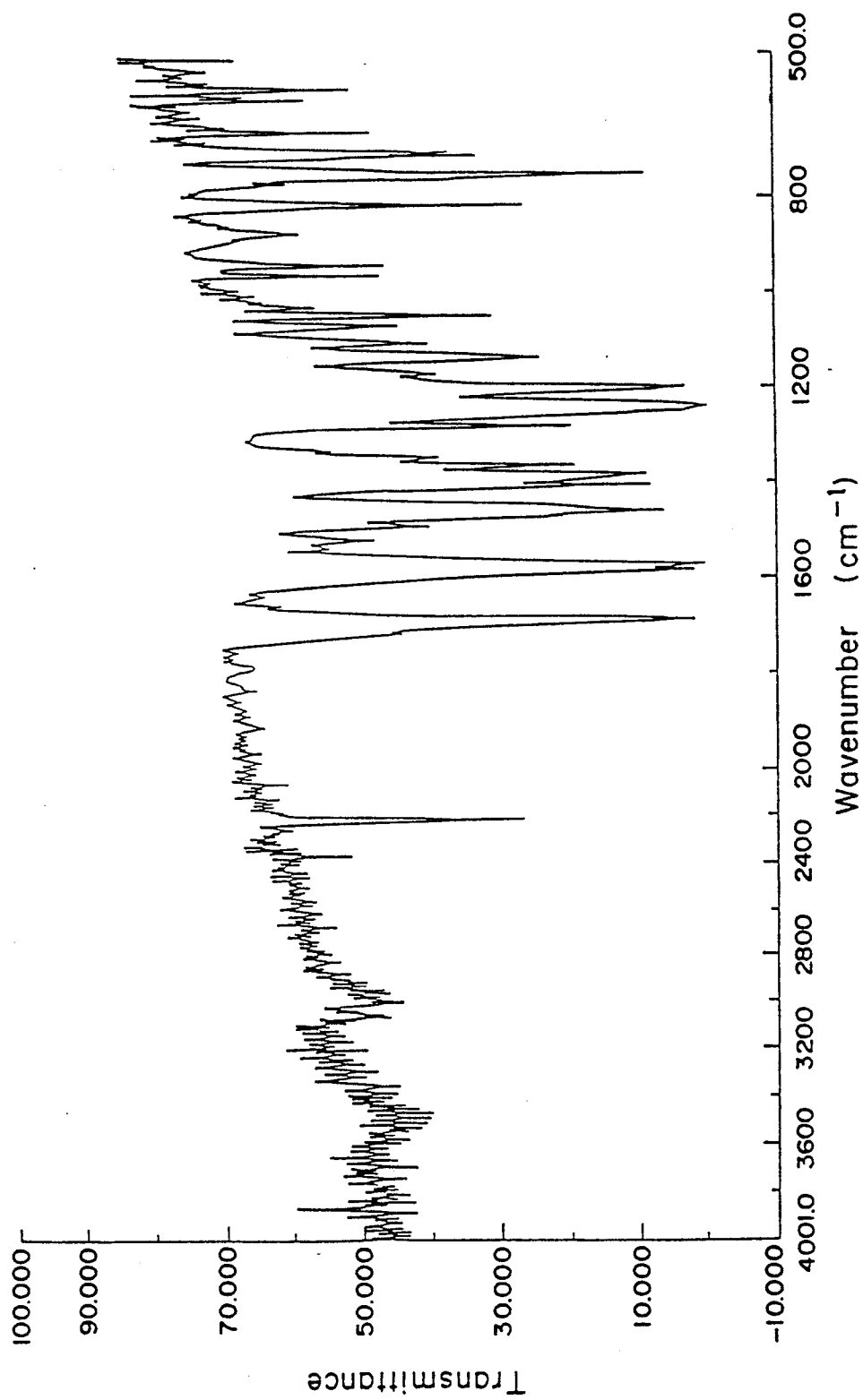
FIG. 9 is a infrared spectrum of the compound 6 according to the present invention.
Figure 10:
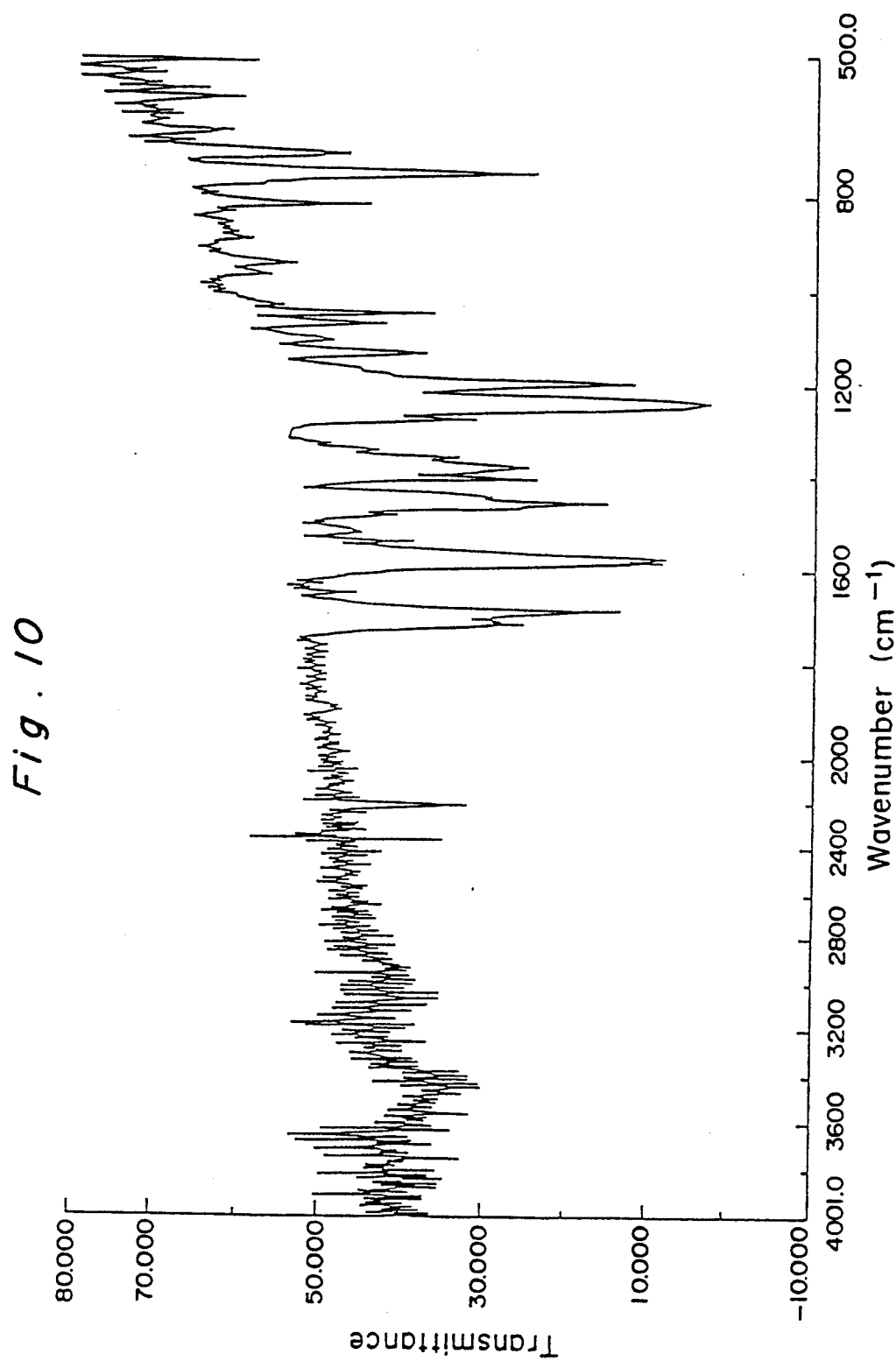
FIG. 10 is a infrared spectrum of the compound 10 according to the present invention.

FIGS. 1, 2, 3, 4 and 5 show near UV-visible light absorption spectra of the compound 1, 2, 6, 7 and 10 respectively. FIGS. 8, 9 and 10 show infrared spectra of the compound 1, 6 and 10 respectively.

EXAMPLES 12 AND 13

These examples illustrate the preparation of the light-resistance evaluation laminate samples which are pieces of magenta printed paper coated with the UV light absorbing coating composition according to the present invention.

Example 12

A transparent UV light absorbing coating composition was prepared form the following formulation.

| Components | Parts by Weight |
|---|---|
| DIANAL LR-1065[a] | 100 |
| compound 1 | 1 |

[a] Forty % acrylic resin solution in methyl ethyl ketone available from Mitsubishi Rayon Co., Ltd.

The UV light absorbing coating composition was applied onto a polyethylene terephthalate (PET) film having a thickness of 100 μm using a bar coater at a final dry coating thickness of about 30 μm. The coated PET film was then dried to provide a transfer sheet material consisting of a PET substrate layer and a UV light absorbing transfer coating layer.

On the other hand, the solid printing of magenta onto a piece of paper was carried out using a color ink jet printer.

Then, onto the printed surface of the paper, the UV light absorbing transfer coating layer surface of the transfer sheet material was laminated so as to cover the printed magenta pattern. The PET substrate layer was then removed to provide a laminate sample A.

Example 13

A laminate sample B was prepared in essentially the same manner as described in Example 12, except that the transparent UV light absorbing composition was prepared form the following formulation.

| Components | Parts by Weight |
|---|---|
| DIANAL LR-1065[a] | 100 |
| compound 6 | 0.5 |
| TINUVIN P328[b] | 0.5 |

[a] Forty % acrylic resin solution in methyl ethyl ketone available from Mitsubishi Rayon Co., Ltd.
[b] UV light absorber available from Ciba-Geigy Ltd.

EXAMPLE 14

This example illustrates the evaluation in light-resistance of the laminate samples prepared in Example 12 and 13.

The laminate samples A, B and comparative sample 1 which was a piece of magenta printed paper prepared as described in example 12 (i.e. The comparative sample 1 was not coated with the UV light absorbing coating composition according to the present invention.) were irradiated for 20 hours on a long life carbon-arc fadeometer (SUGA TEST INSTRUMENTS Co., Ltd.). Light-resistance of the samples were evaluated by visual inspection of their color change. The results are shown in Table 2.

TABLE 2

| Samples | Light-resistance |
|---|---|
| A | good[a] |
| B | good |
| comparative 1 | fail[b] |

[a] No color change was substantially observed.
[b] High degree of color change was observed.

EXAMPLE 15

This example illustrate that the UV light absorbing compound according to the present invention is compatible with the conventional UV light absorbing compounds having λ of about 300 nm to about 380 nm.

Figure 6:
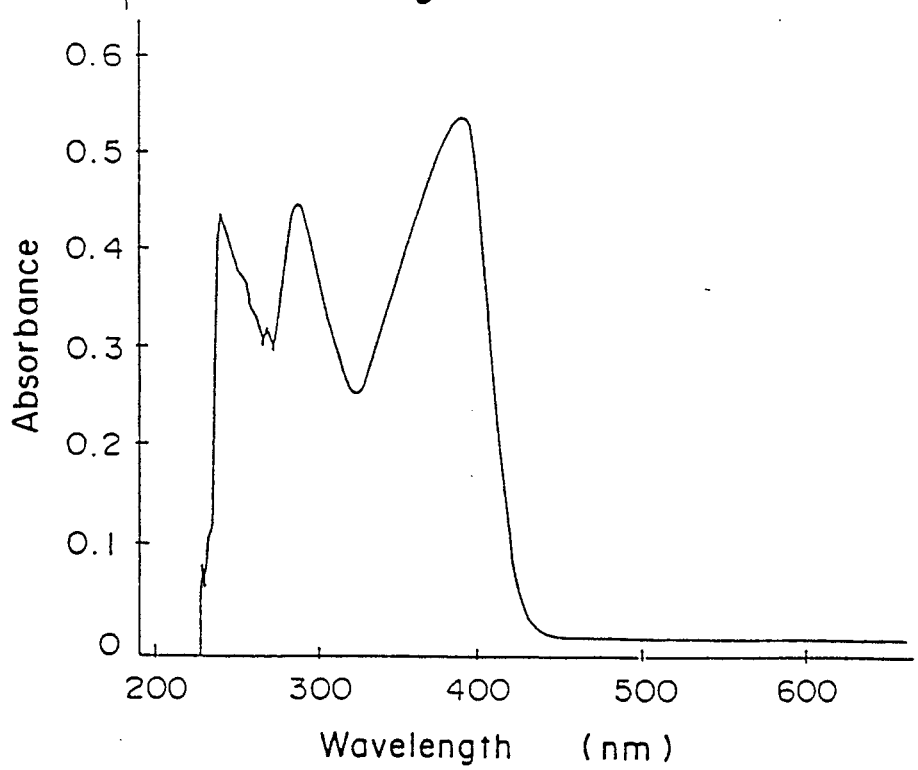
FIG. 6 is a near UV-visible light absorption spectrum of the mixture prepared from compound 1 according to the present invention and benzotriazole UV light absorber at a weight ratio of 1:1.
Figure 7:
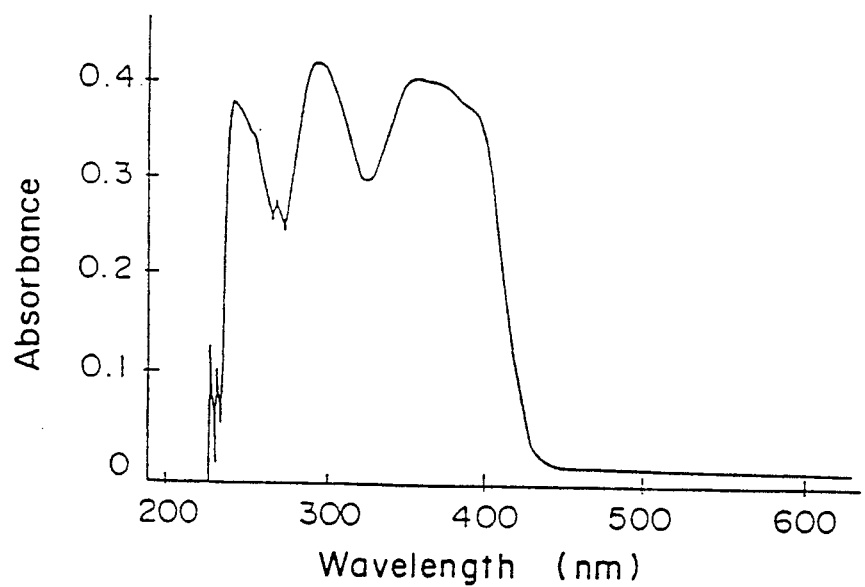
FIG. 7 is a near UV-visible light absorption spectrum of the mixture prepared from compound 1 according to the present invention and benzotriazole UV light absorber at a weight ratio of 1:2.

FIGS. 6 and 7 show near UV-visible light absorption spectra of the mixture prepared from compound 1 and benzotriazole UV light absorber (TINUVIN P328, Ciba-Geigy Ltd.) at a weight ratio of 1:1 and 1:2 respectively. The wide spectral range in absorption between about 250 nm and about 400 nm was the result of the combination use thereof.

What is claimed is:

1. A UV light absorber composition comprising an effective UV wavelength absorbing amount of an indole compound of the general formula:

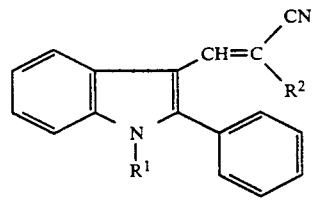

wherein $R^1$ represents a linear or branched alkyl or aralkyl group, and $R^2$ represents —CN or —COOR$^3$, wherein $R^3$ a linear or branched alkyl or aralkyl group having 1–20 carbon atoms, a β-cyanoethyl group, a β-chloroethyl group, a hydroxyalkyl group having 1–20 carbon atoms and an alkoxyalkyl group having 1–20 carbon atoms, as the active ingredient and a carrier acceptable for said UV light absorber composition.

2. The UV light absorbing composition according to claim 1 wherein said indole compound has a $\lambda_{max}$ in the spectral range between about 380 nm and about 400 nm.

3. A resin composition comprising the UV light absorber composition according to claim 1.

4. A coating composition comprising the UV light absorber composition according to claim 1.

* * * * *